US009132132B2

(12) United States Patent
Reddy et al.

(10) Patent No.: US 9,132,132 B2
(45) Date of Patent: Sep. 15, 2015

(54) PHARMACEUTICAL COMPOSITIONS OF LINEZOLID

(75) Inventors: Bandi Parthasaradhi Reddy, Hyderabad (IN); Podili Khadgapathi, Hyderabad (IN); Goli Kamalakar Reddy, Hyderabad (IN); Lekkala Vamshi Krishna, Hyderabad (IN)

(73) Assignee: HETERO RESEARCH FOUNDATION (IN)

( * ) Notice: Subject to any disclaimer, the term of this patent is extended or adjusted under 35 U.S.C. 154(b) by 160 days.

(21) Appl. No.: 13/813,459

(22) PCT Filed: Aug. 29, 2011

(86) PCT No.: PCT/IN2011/000583
§ 371 (c)(1),
(2), (4) Date: Jan. 31, 2013

(87) PCT Pub. No.: WO2012/029074
PCT Pub. Date: Mar. 8, 2012

(65) Prior Publication Data
US 2013/0274262 A1 Oct. 17, 2013

(30) Foreign Application Priority Data
Sep. 2, 2010 (IN) ............................ 2557/CHE/2010

(51) Int. Cl.
*A61K 31/535* (2006.01)
*A61K 31/5377* (2006.01)
*A61K 9/20* (2006.01)

(52) U.S. Cl.
CPC .......... *A61K 31/5377* (2013.01); *A61K 9/2027* (2013.01); *A61K 9/2077* (2013.01); *A61K 9/2095* (2013.01)

(58) Field of Classification Search
CPC ............ A61K 31/5377; A61K 9/2027; A61K 9/2077; A61K 9/2095
USPC ........................................ 514/236.8; 544/137
See application file for complete search history.

(56) References Cited

U.S. PATENT DOCUMENTS

| 5,688,792 | A | 11/1997 | Barbachyn et al. | |
| 6,514,529 | B2 * | 2/2003 | Yamamoto et al. | 424/465 |
| 6,559,305 | B1 * | 5/2003 | Bergren | 544/137 |
| 7,714,128 | B2 | 5/2010 | Rao et al. | |
| 7,718,800 | B2 * | 5/2010 | Rao et al. | 544/137 |
| 7,732,597 | B2 * | 6/2010 | Rao et al. | 544/137 |
| 7,989,618 | B2 * | 8/2011 | Vladiskovic et al. | 544/137 |
| 2006/0111350 | A1 | 5/2006 | Aronhime et al. | |
| 2007/0020329 | A1 * | 1/2007 | Tenengauzer et al. | 424/464 |
| 2007/0104785 | A1 | 5/2007 | Navale et al. | |
| 2008/0090824 | A1 * | 4/2008 | Rao et al. | 514/236.8 |

FOREIGN PATENT DOCUMENTS

| WO | 2007012082 A2 | 1/2007 |
| WO | 2010026597 A1 | 3/2010 |

OTHER PUBLICATIONS

Bele et al., "Mechanism of disintegrant action of polacrilin potassium: Swelling or wicking?", 2012, Acta Pharmaceutica Sinica B, 2(1), pp. 70-76.*
Rutesh H. Dave, "Overview of pharmaceutical excipients used in tablets and capsules", Oct. 24, 2008, Published on Drug Topics (http://drugtopics.modernmedicine.com), pp. 1-15.*
Remington: The Science and Practice of Pharmacy, May 2005, Lippincott Williams & Wilkins, Edition 21, Chapter 45 on pp. 889-928 and Chapter 55 on pp. 1058-1092.*
International Search Report and Written Opinion; Unternational application No. PCT/IN11/00583; International Filing Date Aug. 29, 2011; Date of Mailing Mar. 20, 2012; 10 pages.

* cited by examiner

*Primary Examiner* — My-Chau T Tran
(74) *Attorney, Agent, or Firm* — Cantor Colburn LLP

(57) ABSTRACT

The present invention relates to stable pharmaceutical compositions comprising linezolid crystalline Form III with one or more pharmaceutically acceptable excipients, wherein the composition retains linezolid in its original crystalline form.

8 Claims, 10 Drawing Sheets

PHARMACEUTICAL COMPOSITIONS OF LINEZOLID

CROSS-REFERENCE TO RELATED APPLICATIONS

This application is a 371 of PCT/IN2011/000583 filed Aug. 29, 2011, which claims the benefit of priority to Indian application No. 2557/CHE/2010, filed on Sep. 2, 2010; under the provisions of 35 U.S.C. 119 and the International Convention for the protection of Industrial Property, which are incorporated herein by reference.

PRIORITY DETAILS

This patent application claims priority to Indian application number 2557/CHE/2010, filed Sep. 2, 2010, the contents of which are incorporated by reference here in.

BACKGROUND OF THE INVENTION

Linezolid is a synthetic antibacterial agent. Chemically, it is (S)—N-[[3-[3-Fluoro-4-(4-morpholinyl)phenyl]-2-oxo-5-oxazolidinyl]methyl]-acetamide. The empirical formula is $C_{16}H_{20}FN_3O_4$. Its molecular weight is 337.35.

Linezolid is used in the treatment of vancomycin-resistant *enterococcus faecium* infections; nosocomial pneumonia; complicated skin and skin structure infections including diabetic foot infections, without concomitant osteomyelitis; uncomplicated skin and skin structure infections and community acquired pneumonia.

Linezolid is sold in the U.S. under the brand name(s) of ZYVOX® I.V. Injection, ZYVOX Tablets, and ZYVOX for Oral Suspension. Tablets were given two to three times a day.

Linezolid and its salts are described in U.S. Pat. No. 5,688,792. Crystalline form I and II are known polymorphs of Linezolid. Crystalline form I of linezolid was described by J. Med. Chem. 39(3), 673-679, 1996.

U.S. Pat. No. 6,559,305 discloses a crystalline linezolid form II.

WO2007/102082 assigned to Glenmark Pharmaceuticals Ltd discloses compositions of Linezolid crystalline Form II containing lactose-based water soluble excipient.

In the recent years, a new polymorph of linezolid, namely form III, was discovered and described in U.S. Pat. No. 7,714,128. The crystalline form III was characterized by an x-ray powder diffraction spectrum having peaks expressed as 2θ at about 7.6, 9.6, 13.6, 14.9, 18.2, 18.9, 21.2, 22.3, 25.6, 26.9, 27.9 and 29.9 degrees.

U.S. Publication no. 2007/0104785 discloses a manufacture of the solid oral dosage form of linezolid Form III. It describes a gelling potential of linezolid Form III which affects the reproducibility of dissolution. The manufacturing of the dosage form with reproducible dissolution profile was achieved by using effervescent couple (or) by incorporating water insoluble polymers (or) by adding clays in the dosage form (or) combinations thereof.

WO 2010/026597 assigned to Hetero discloses a multiparticulate composition which requires forming a core in the form of beadlet or pellet manufactured by extrusion and spheronization method, where the core comprises linezolid form III, one or more binders, and one or more disintegrants. Both processes require either special material or equipment which are not desirable for commercial production.

There is a need to develop a composition and its process for manufacturing a solid unit dosage form comprising linezolid form III which retains its polymorphic form and stable during manufacturing process and throughout the shelf life.

SUMMARY OF THE INVENTION

A first aspect of the present invention provides stable pharmaceutical composition comprising linezolid crystalline Form III with one or more pharmaceutically acceptable excipients, prepared by dry granulation process, wherein the composition retains linezolid in its original crystalline form.

Another aspect of the present invention provides stable pharmaceutical composition comprising a therapeutically effective amount of a linezolid form III, polacrilin potassium as disintegrant, hydroxypropylmethyl cellulose as binder and optionally one or more additional excipients, wherein the composition retains linezolid in its crystalline form.

Another aspect of the present invention is to provide a stable pharmaceutical composition containing one or more combination of excipients having different functional properties such as sodium carboxy methyl cellulose, calcium carboxy methyl cellulose, di calcium phosphate, sodium startch glycolate, lactose, microcrystalline cellulose, polacrilin potassium, polyvinyl pyrollidone, hydroxy propyl methyl cellulose, alginic acid, sodium alginate, magnesium stearate, sodium stearyl fumarate, colloidal silicon dioxide suitable for stable compositions without polymorphic form conversion.

The present invention also provides process for preparing stable pharmaceutical composition comprising linezolid form III, polacrilin potassium as disintegrant and at least one pharmaceutically acceptable excipient, using wet granulation, dry granulation, spray granulation or direct compression to develop a solid dosage form without polymorphic form conversion.

Another aspect of the present invention provides process for preparing stable pharmaceutical composition comprising linezolid form III and at least one pharmaceutically acceptable excipient by wet granulation using about 10% w/w of water (based on total weight of the core tablet) as granulating solvent, wherein the composition retains more than 80% linezolid form III.

Another aspect of the present invention is directed to method of preparing a solid pharmaceutical composition by admixing linezolid from III with pharmaceutically acceptable excipients to provide a mixture and directly compressing the mixture.

Another aspect of the present invention is directed to method of preparing a solid pharmaceutical composition comprising linezolid form III by dry granulation.

In another aspect of the present invention linezolid form III is dry granulated with lactose monohydrate, hydroxypropylmethyl cellulose and/or starch, polacrilin potassium, magnesium stearate to develop a stable formulation without polymorphic form conversion.

Preferred aspect of the present invention involves dry granulating linezolid form III with polacrilin potassium as disintegrant with one or more pharmaceutically acceptable excipients to develop a stable formulation without polymorphic form conversion.

Another aspect of the present invention provides process for preparing stable pharmaceutical composition comprising linezolid form III, polacrilin potassium as disintegrant, microcrystalline cellulose as diluent and optionally one or more pharmaceutically acceptable excipients by dry granulation, wherein the composition retains linezolid in its crystalline form III.

DETAILED DESCRIPTION OF THE INVENTION

"Composition" or "formulation" as used here synonymously for solid oral dosage forms such as tablets, capsules, sachets etc.

Stable composition, according to the present invention means a composition containing linezolid having more than 80% crystallinity in Form III, preferably more than 85% crystallinity in Form III, and more preferably more than 95% crystallinity in Form III determined by an instrumental test, for example, by XRD, IR, TGA, etc. during manufacturing process and/or under a storage condition (shelf live).

The present aim of the invention is to develop a stable linezolid formulation using various combinations of excipients without converting polymorphic form of the active ingredient in the dosage form.

According to one aspect of the present invention, compatibility studies with various excipients were done to develop a stable formulation that retains its polymorphic form.

Excipient selection depends on various factors, such as, the choice of active ingredient percentage, the objectives of the tablet formulation development and method of manufacture. The foremost property of each excipient is that it must posses compatibility with active ingredient without affecting its polymorphic form Another aspect of the present invention is suitable combinations of excipients having different functional properties such as sodium carboxy methyl cellulose, calcium carboxy methyl cellulose, di calcium phosphate, sodium startch glycolate, lactose monohydrate, lactose impalable, polacrilin potassium, polyvinyl pyrollidone, hydroxy propyl methyl cellulose, alginic acid, sodium alginate, magnesium stearate, sodium stearyl fumarate, colloidal silicon dioxide, are studied to develop a stable formulation without polymorphic form conversion.

In another aspect of the present invention, there is provided stable pharmaceutical composition comprising linezolid with hydroxypropylmethyl cellulose as a binder and polacrilin potassium as a disintegrant, and optionally one or more additional excipients.

A pharmaceutical composition of the present invention may also comprise one or more other excipients such as a diluent, a glidant and a lubricant.

The pharmaceutical composition according to the present invention are oral solid dosage forms such as tablet, a caplet, a pellet, a capsule, granules, a pill, powder or a sachet. Preferably the pharmaceutical composition is in the form of a tablet.

Preferably, linezolid used in the oral solid pharmaceutical composition is crystalline form III.

Preferably, the pharmaceutically acceptable excipients in accordance with the invention include at least one binder and/or at least one disintegrant, and/or at least one diluent and/or at least one lubricant and/or at least one stabiliser.

Preferably, the binder includes hydroxypropyl methylcellulose (hydroxypropylmethyl cellulose), polyvinylpyrrolidone k-30, hydroxypropyl cellulose (low-substituted), starch or mixtures thereof and more preferable binder is hydroxypropylmethyl cellulose and/or starch.

Preferably, the disintegrant include sodium starch glycolate, croscarmellose sodium, polacrilin potassium and crosslinked polyvinyl pyrrolidone or mixtures thereof and more preferable disintegrant is polacrilin potassium.

Preferably, the diluent include mannitol, sorbitol, xylitol, lactose monohydrate, microcrystalline cellulose, light magnesium carbonate, dicalcium phosphate, tribasic calcium phosphate, calcium sulphate or mixture thereof, and more preferable diluent is lactose monohydrate and/or light magnesium carbonate.

Preferably, the lubricant includes magnesium stearate, zinc stearate, calcium stearate, sodium stearyl fumarate and stearic acid or mixtures thereof and more preferable lubricant is magnesium stearate. Preferably, the glidant includes colloidal anhydrous silica.

Other ingredients such as stabilizers and antiadherants, conventionally used for pharmaceutical formulations may also be included in the present formulation.

In another aspect of the present invention, the tablets were manufactured using wet granulation, direct compression, dry granulation (slugging) to develop a stable formulation without polymorphic form conversion.

Another aspect of the present invention provides wet granulation process with different concentrations of water such as 10% w/w, 20% w/w, 30% w/w as granulation solvent for preparation of the core tablet.

Wet granulation with about 10% w/w of water (based on total weight of core tablet) is found to be suitable for developing a stable formulation.

Another aspect of the present invention is directed to method of preparing a solid pharmaceutical composition comprising admixing linezolid from III with pharmaceutically acceptable excipients and compressing the mixture in to tablets.

In another aspect of the present invention preferably, dry granulation by slugging to develop a stable formulation without polymorphic form conversion of linezolid.

According to another aspect of the present invention, there is provided a process for preparing stable pharmaceutical composition which comprises mixing linezolid from III, hydroxypropylmethyl cellulose as a binder and polacrilin potassium as a disintegrant, and optionally one or more additional excipients and compressing in to tablet.

Preferably, the pharmaceutical compositions prepared according to process of the invention are oral solid dosage forms such as tablet, a caplet, a pellet, a capsule, granules, a pill, powder or a sachet.

The tablet may be optionally coated with a coating agent. The film coating is non functional and provides good appearance to the final dosage form.

The preferred embodiment of the invention suitable for forming linezolid tablet comprising in parts by weight from about 60% to about 90% linezolid, from about 1% to about 30% lactose monohydrate, from about 0.3% to about 20% hydroxypropylmethyl cellulose and/or starch, from about 0.2% to about 8% polacrilin potassium, from about 0.5% to about 5% magnesium stearate. Optionally additional excipient/s such as diluents, binders, disintegrants, lubricants, glidants, fillers or mixtures thereof may be used.

The invention is further exemplified with following examples and is not intended to limit the scope of the invention. It is obvious to those skilled in the art to find out the composition for other dosage forms and substitute the equivalent excipients as described in this specification or with the one known to the industry.

Example 1

| S. No | Ingredients | Mg/Tablet |
|---|---|---|
| | Intragranular | |
| 1 | Linezolid (Form III) | 600 |
| 2 | Lactose monohydrate | 70 |
| 3 | Hydroxypropylmethyl cellulose | 12 |
| 4 | Polacrilin potassium | 5 |
| 5 | Magnesium stearate | 10 |

-continued

| S. No | Ingredients | Mg/Tablet |
|---|---|---|
| | Extragranular Ingredients | |
| 6 | Lactose monohydrate | 140 |
| 7 | Silica colloidal anhydrous | 10 |
| 8 | Polacrilin potassium | 5 |
| 9 | Magnesium stearate | 8 |
| 10 | Opadry White 03B58895 | 13.00 |
| 11 | Purified water | qs |
| | Total weight | 873 |

Brief Manufacturing Process:

Linezolid, lactose monohydrate, hydroxypropylmethyl cellulose, polacrilin potassium and magnesium stearate are sifted through suitable mesh and blended. The dry mix is granulated by slugging method. The formed slug mass was milled and passed through suitable screen. The blend is pre-lubricated and lubricated with lactose monohydrate, silica colloidal anhydrous, polacrilin potassium, magnesium stearate and compressed into a tablet using appropriate tooling or the granules were filled into capsules/sachets.

Example 2

| S. No | Ingredients | Mg/Tablet |
|---|---|---|
| | Intragranular | |
| 1 | Linezolid (Form III) | 600 |
| 2 | Lactose monohydrate | 25 |
| 3 | Light magnesium carbonate | 25 |
| 4 | Hydroxypropylmethyl cellulose | 12 |
| 5 | Polacrilin potassium | 5 |
| 6 | Magnesium stearate | 10 |
| | Extragranular Ingredients | |
| 7 | Lactose monohydrate | 145 |
| 8 | Silica colloidal anhydrous | 10 |
| 9 | Polacrilin potassium | 8 |
| 10 | Magnesium stearate | 8 |
| | Total weight | 848 |

Brief Manufacturing Process:

The dry granules were prepared with the procedure described in the example 1. The lubricated blend was compressed into tablets using appropriate tooling.

Example 3

| S. No | Ingredients | Mg/Tablet |
|---|---|---|
| | Intragranular | |
| 1 | Linezolid (Form III) | 600 |
| 2 | Lactose monohydrate | 25 |
| 3 | Light magnesium carbonate | 10 |
| 4 | Hydroxypropylmethyl cellulose | 12 |
| 5 | Magnesium stearate | 10 |
| | Extragranular Ingredients | |
| 6 | Lactose monohydrate | 165 |
| 7 | Silica colloidal anhydrous | 10 |
| 8 | Polacrilin potassium | 3 |
| 9 | Magnesium stearate | 8 |
| | Total weight | 843 |

Brief Manufacturing Process:

The dry granules were prepared with the procedure described in the example 1. The lubricated blend was compressed into tablets using appropriate tooling.

Example 4

| S. No | Ingredients | Mg/Tablet |
|---|---|---|
| | Intragranular | |
| 1 | Linezolid Form III | 600 |
| 2 | Microcrysatlline cellulose | 25 |
| 3 | Light magnesium carbonate | 25 |
| 4 | Hydroxypropylmethyl cellulose | 24 |
| 5 | Polacrilin potassium | 5 |
| 6 | Magnesium stearate | 10 |
| | Extragranular Ingredients | |
| 7 | Microcrysatlline cellulose | 135 |
| 8 | Silica colloidal anhydrous | 10 |
| 9 | Polacrilin potassium | 8 |
| 10 | Magnesium stearate | 8 |
| | Total weight | 850 |

Brief Manufacturing Process:

The dry granules were made with the procedure described in the example 1. The lubricated blend was compressed into tablets using appropriate tooling.

Example 5-6

| S. No | Ingredients | Example-5 Mg/tablet | Example-6 Mg/tablet |
|---|---|---|---|
| | Intragranular | | |
| 1 | Linezolid (Form III) | 600 | 600 |
| 2 | Lactose monohydrate | 25 | 25 |
| 3 | Starch 1500 | 85 | 85 |
| 4 | Hydroxypropylmethyl cellulose | 3 | 3 |
| 5 | Magnesium stearate | 4 | 4 |
| | Extra granular | | |
| 6 | Starch 1500 | 60 | 60 |
| 7 | Silica colloidal anhydrous | 10 | 10 |
| 8 | Polacrilin potassium | 42 | — |
| 9 | Croscarmellose sodium | — | 42 |
| 10 | Magnesium stearate | 4 | 4 |
| | TOTAL WEIGHT | 833 | 833 |

Brief Manufacturing Process:

The dry granules were made with the procedure described in the example 1. The lubricated blend was compressed into tablets using appropriate tooling.

Example 7

| S. No | Ingredients | Mg/Tablet |
|---|---|---|
| | Intragranular | |
| 1. | Linezolid (Form III) | 600 |
| 2. | Lactose monohydrate | 110 |
| 3. | Hydroxypropylmethyl cellulose | 3 |

-continued

| S. No | Ingredients | Mg/Tablet |
|---|---|---|
| 4. | Magnesium stearate | 4 |
| 5. | Water | 10% w/w |
| | Extragranular Ingredients | |
| 6. | Lactose monohydrate | 60 |
| 7. | Silica colloidal anhydrous | 10 |
| 8. | Polacrilin potassium | 39 |
| 9. | Magnesium stearate | 4 |
| | Total weight | 830 |

Brief Manufacturing Process:

Intragranular excipients were granulated using 10% w/w of water as granulation solvent to obtain the granules. Granules were dried, lubricated and finally compressed in to tablets.

Example 8 And 9

Tablets were prepared exactly to example 7 by wet granulation using 20% w/w and 30% w/w of water as granulation solvent and subjected to XRD studies.

Figure 1:
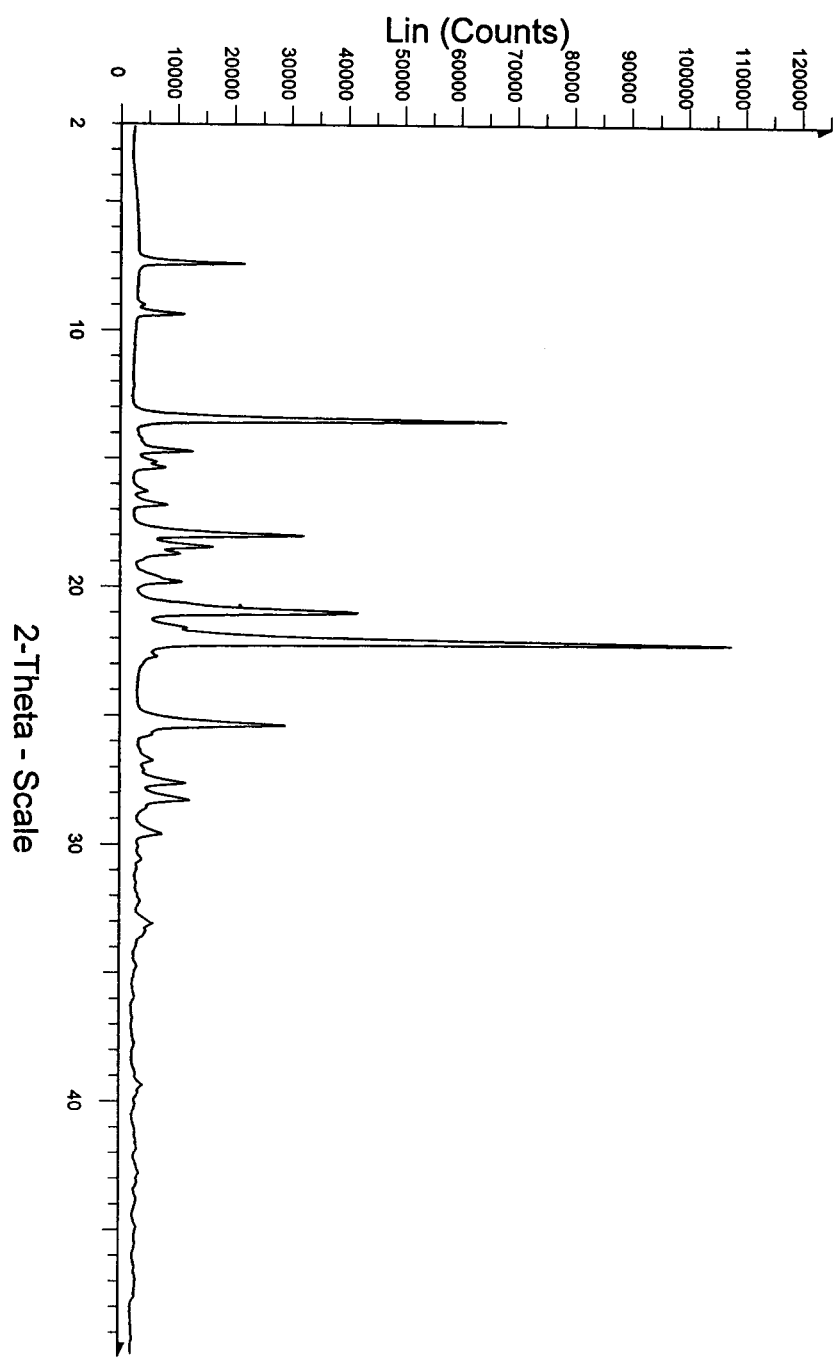
FIG. 1: XRD diffractogram of the linezolid form III.
Figure 2:
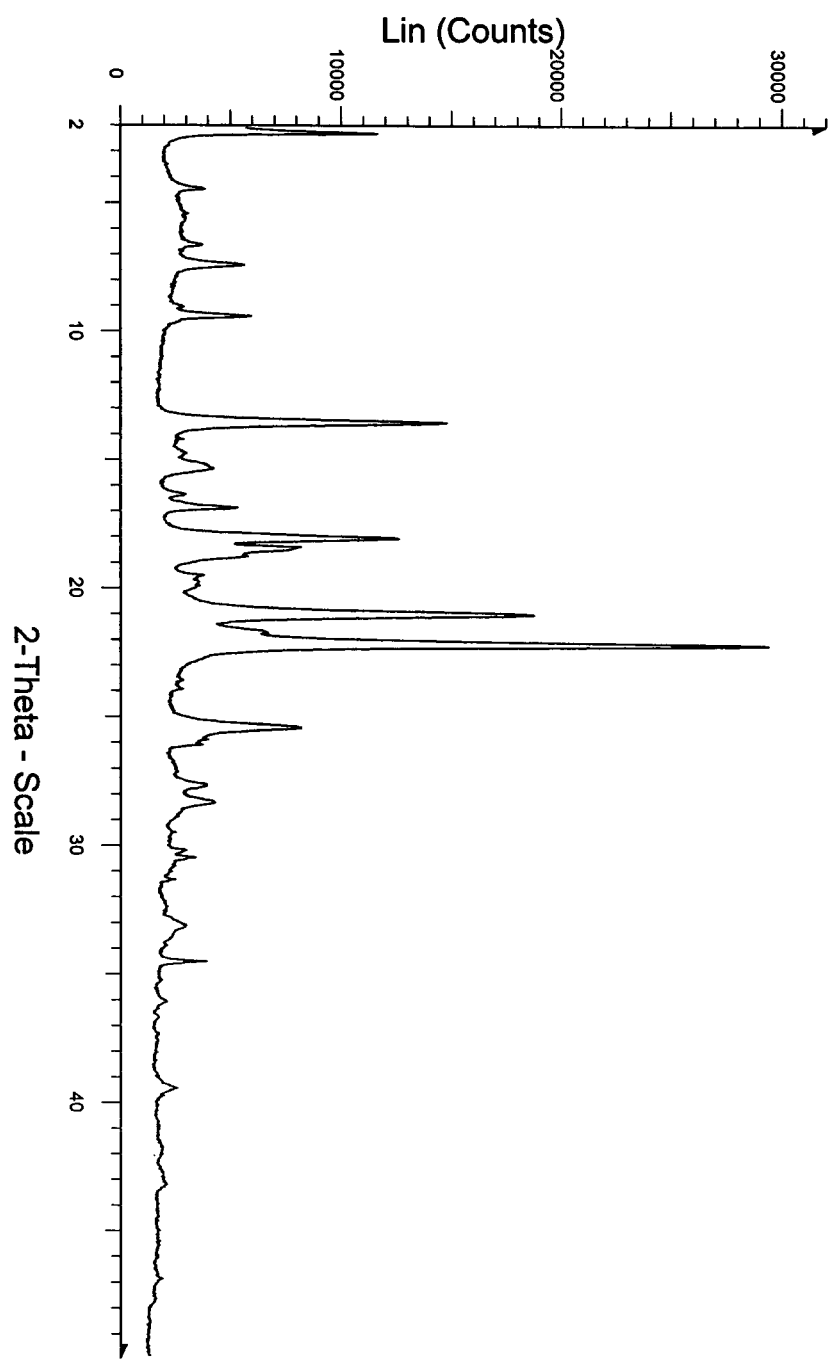
FIG. 2: XRD diffractogram of the linezolid form III pharmaceutical compositions prepared by wet granulation using the concentration of 10% w/w of water.
Figure 3:
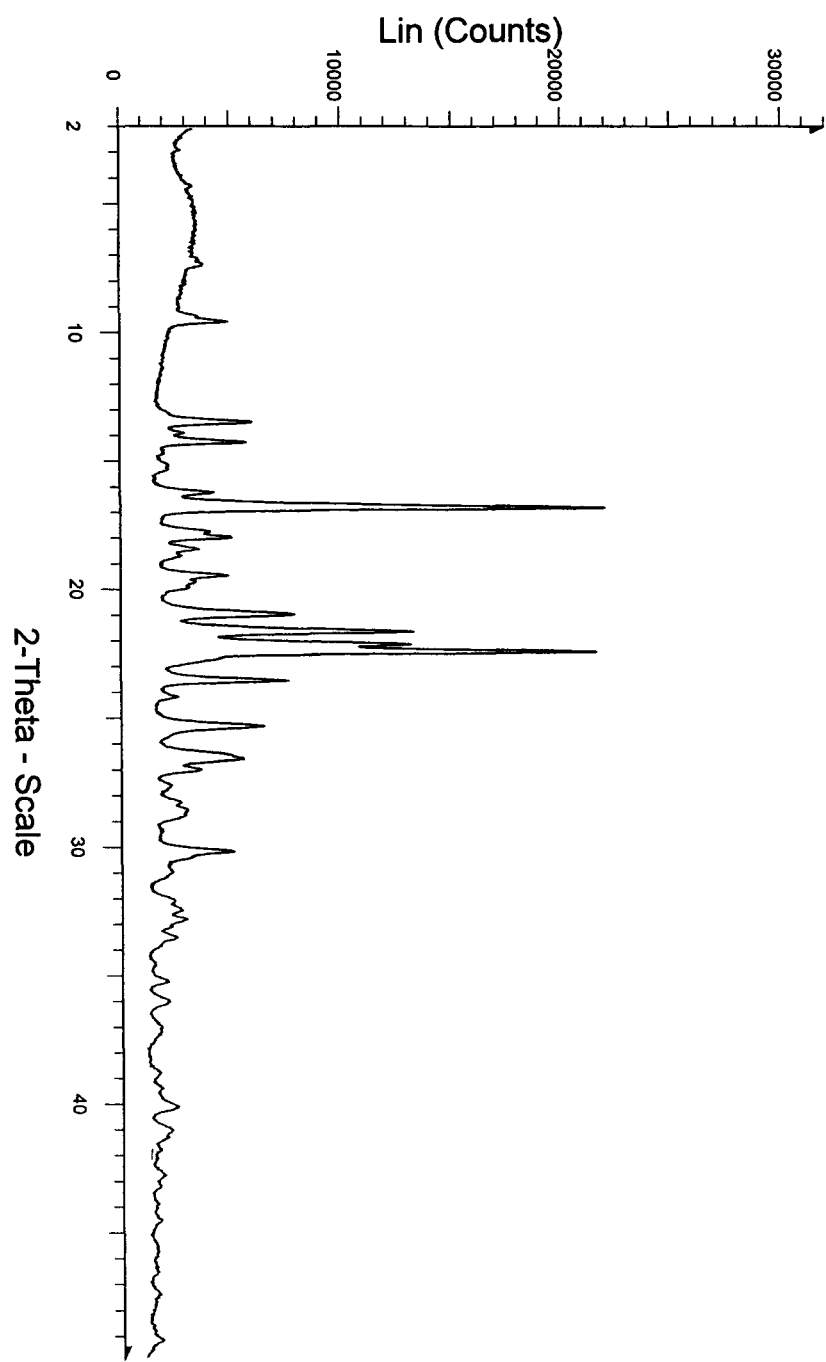
FIG. 3: XRD diffractogram of the linezolid form III pharmaceutical compositions prepared by wet granulation with 20% w/w of water.
Figure 4:
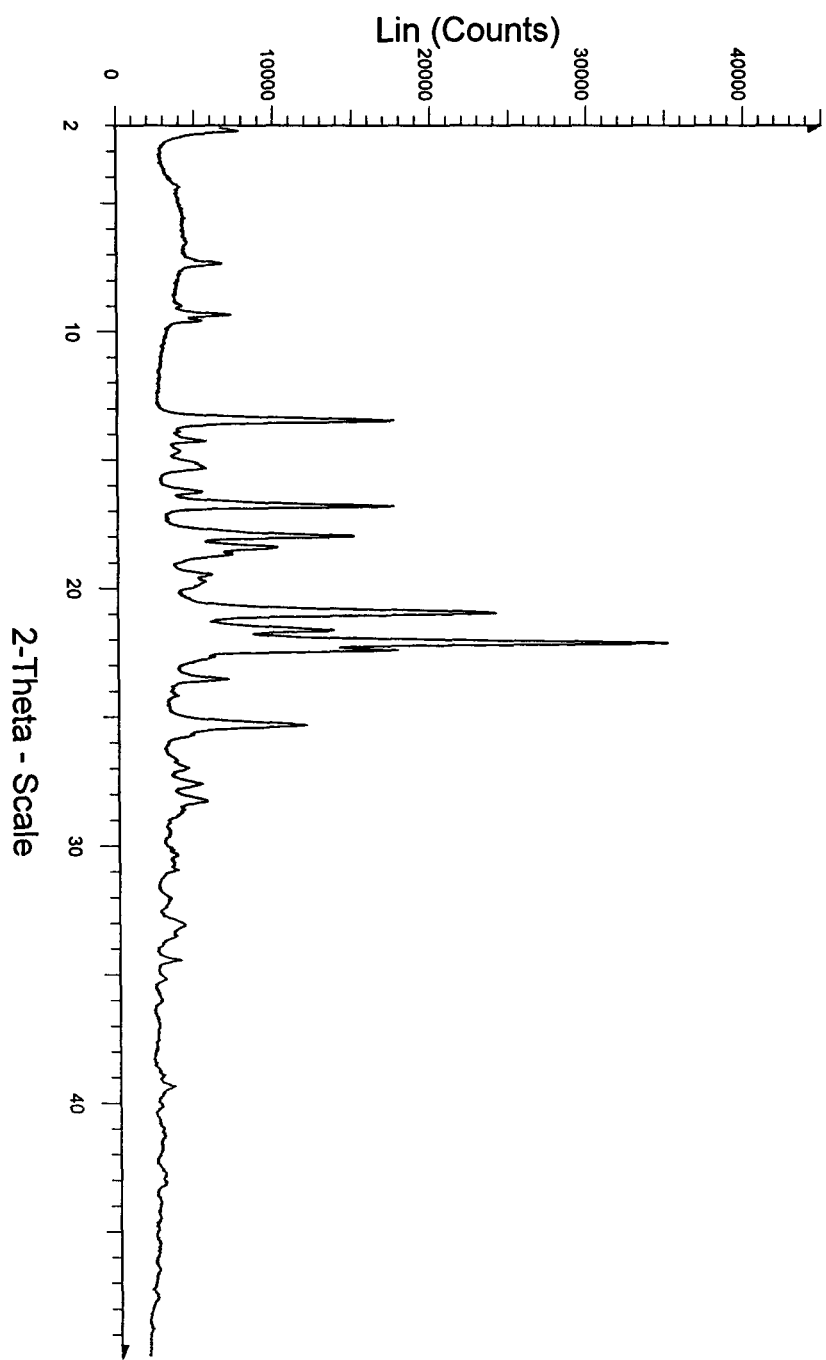
FIG. 4: XRD diffractogram of the linezolid form III pharmaceutical compositions prepared by wet granulation with 30% w/w of water.
Figure 5:
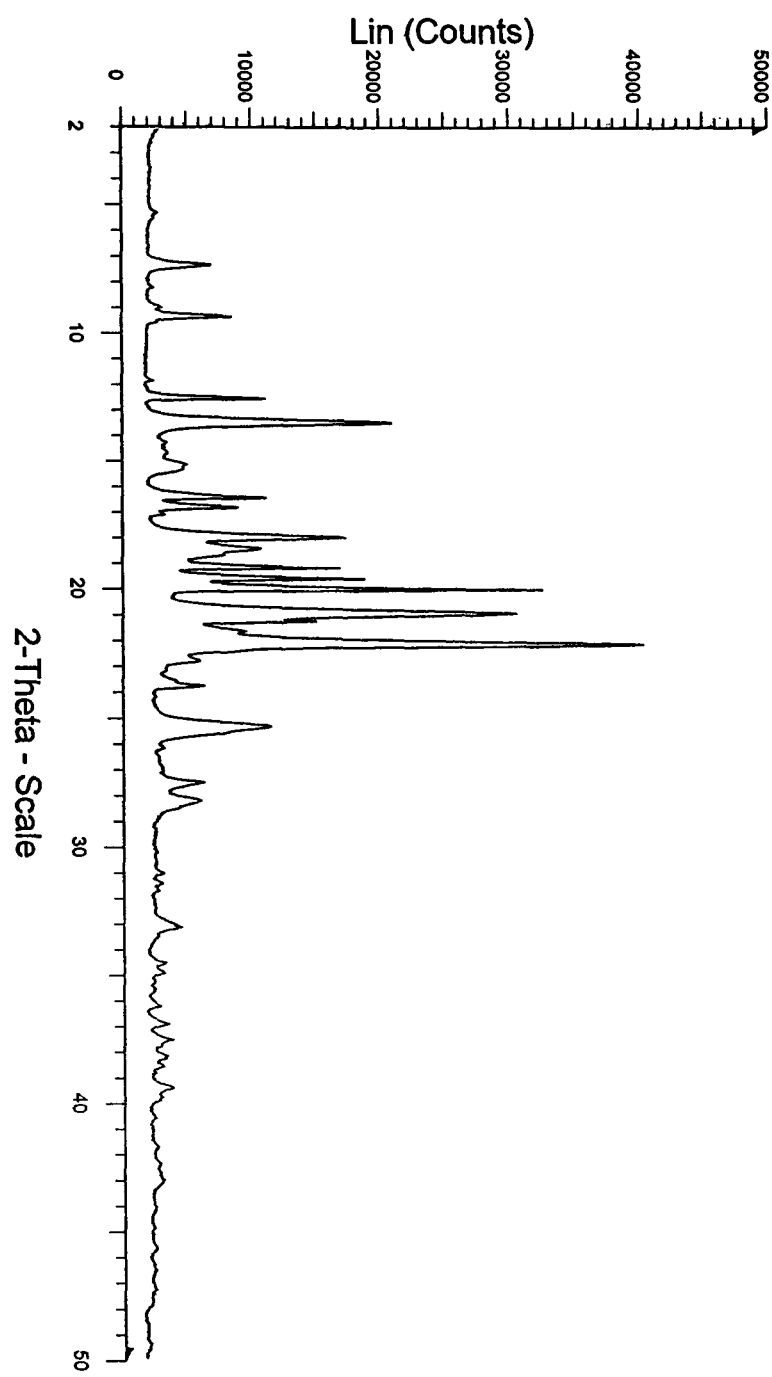
FIG. 5: XRD diffractogram of the linezolid form III at room temperature.
Figure 6:
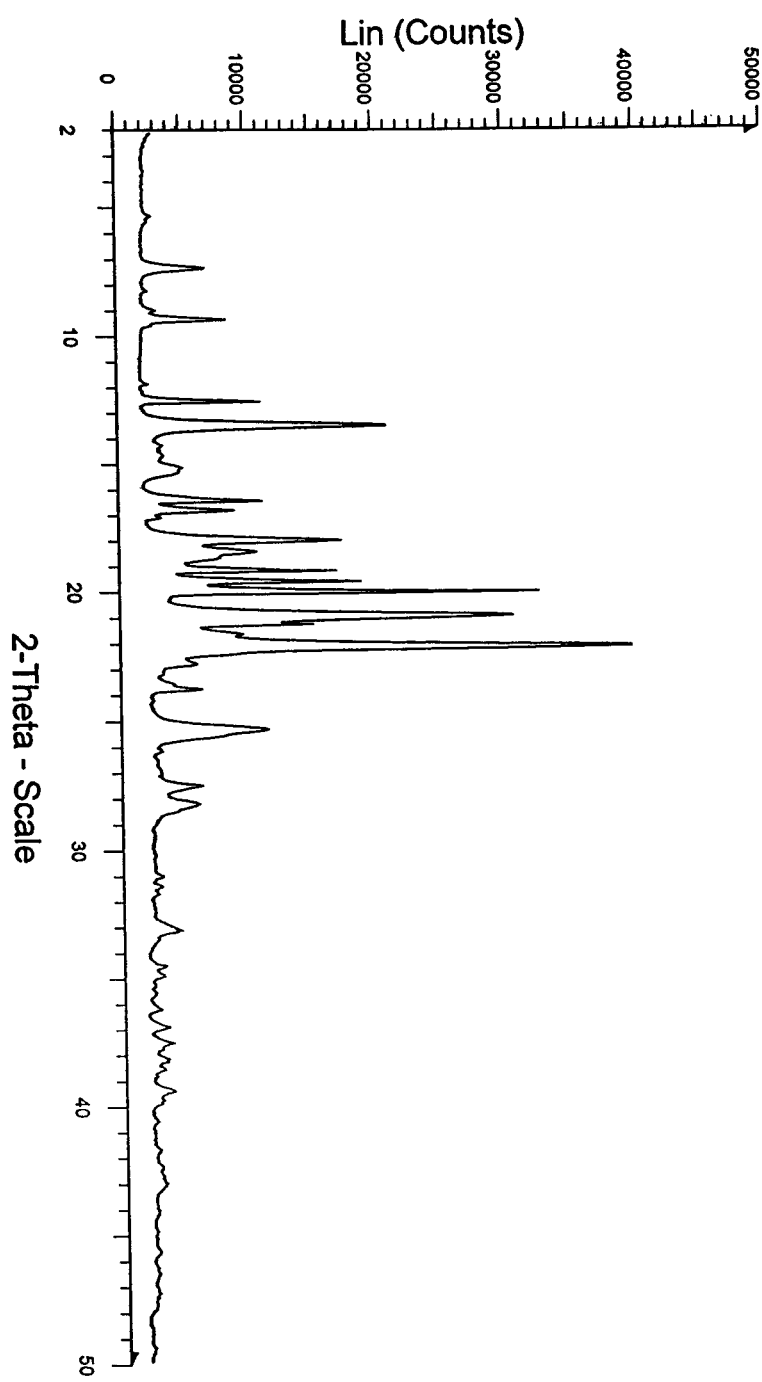
FIG. 6: XRD diffractogram of the linezolid form III pharmaceutical composition prepared by dry granulation at 40° C./75% RH (relative humidity) for 1 month.
Figure 7:
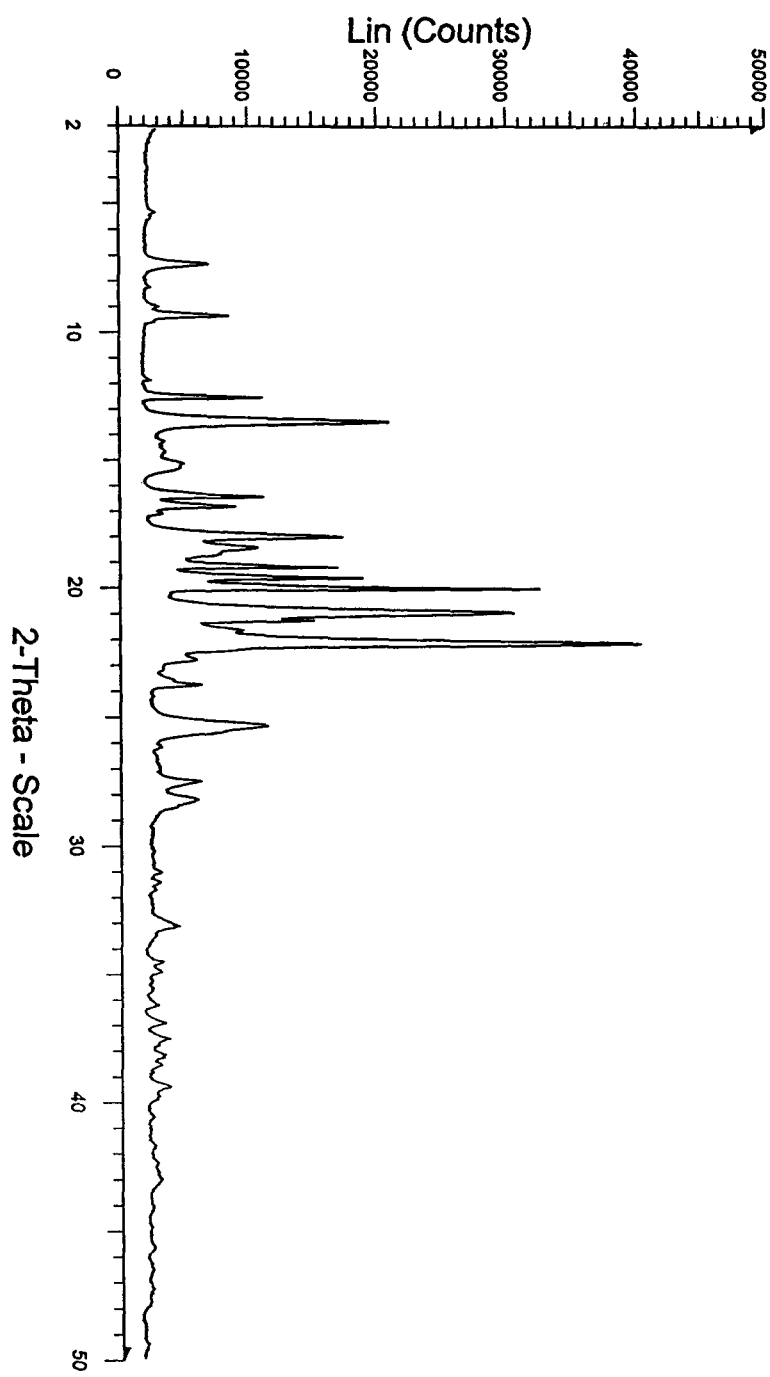
FIG. 7: XRD diffractogram of the linezolid form III pharmaceutical composition prepared by dry granulation at 40° C./75% RH for 2 months.
Figure 8:
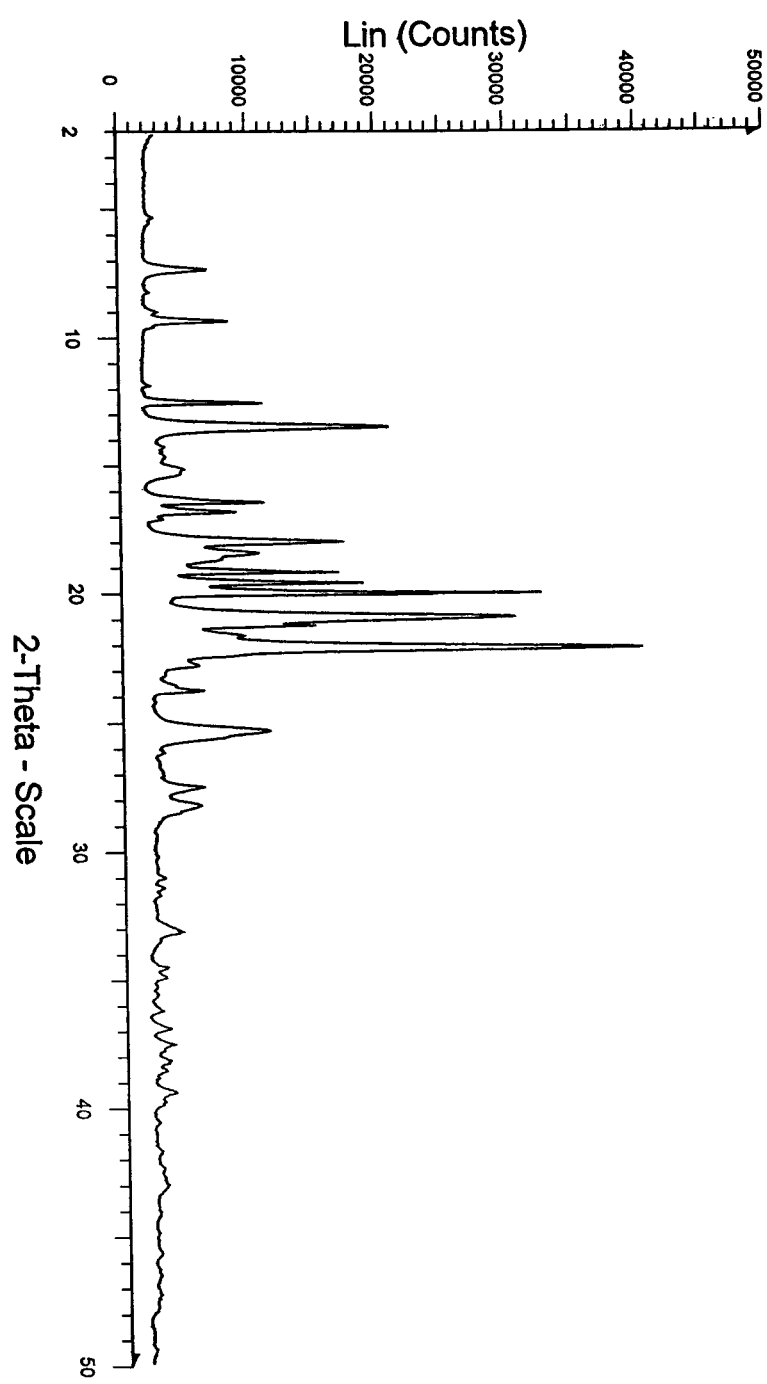
FIG. 8: XRD diffractogram of the linezolid form III pharmaceutical composition prepared by dry granulation at 40° C./75% RH for 3 months.
Figure 9:
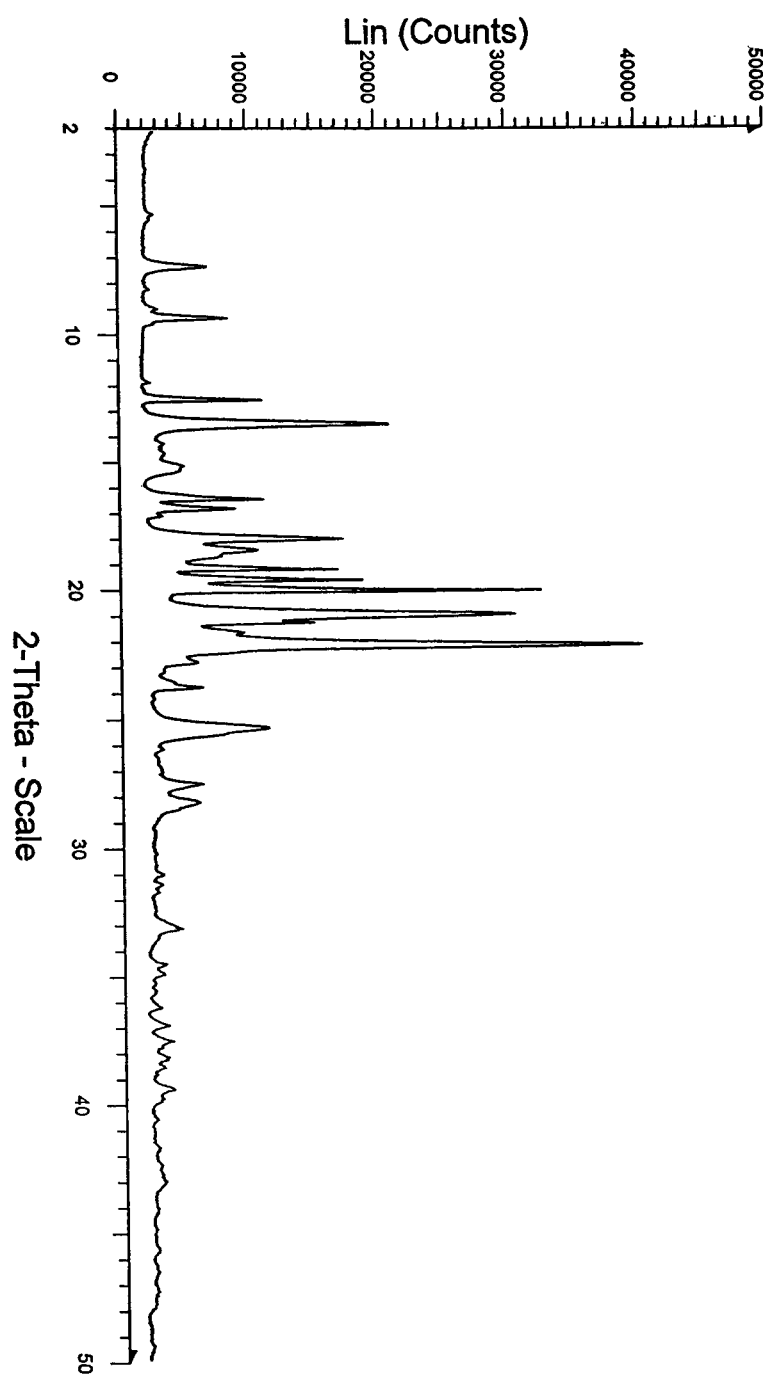
FIG. 9: XRD diffractogram of the linezolid form III pharmaceutical composition prepared by dry granulation at 25° C./60% RH for 3 months.
Figure 10:
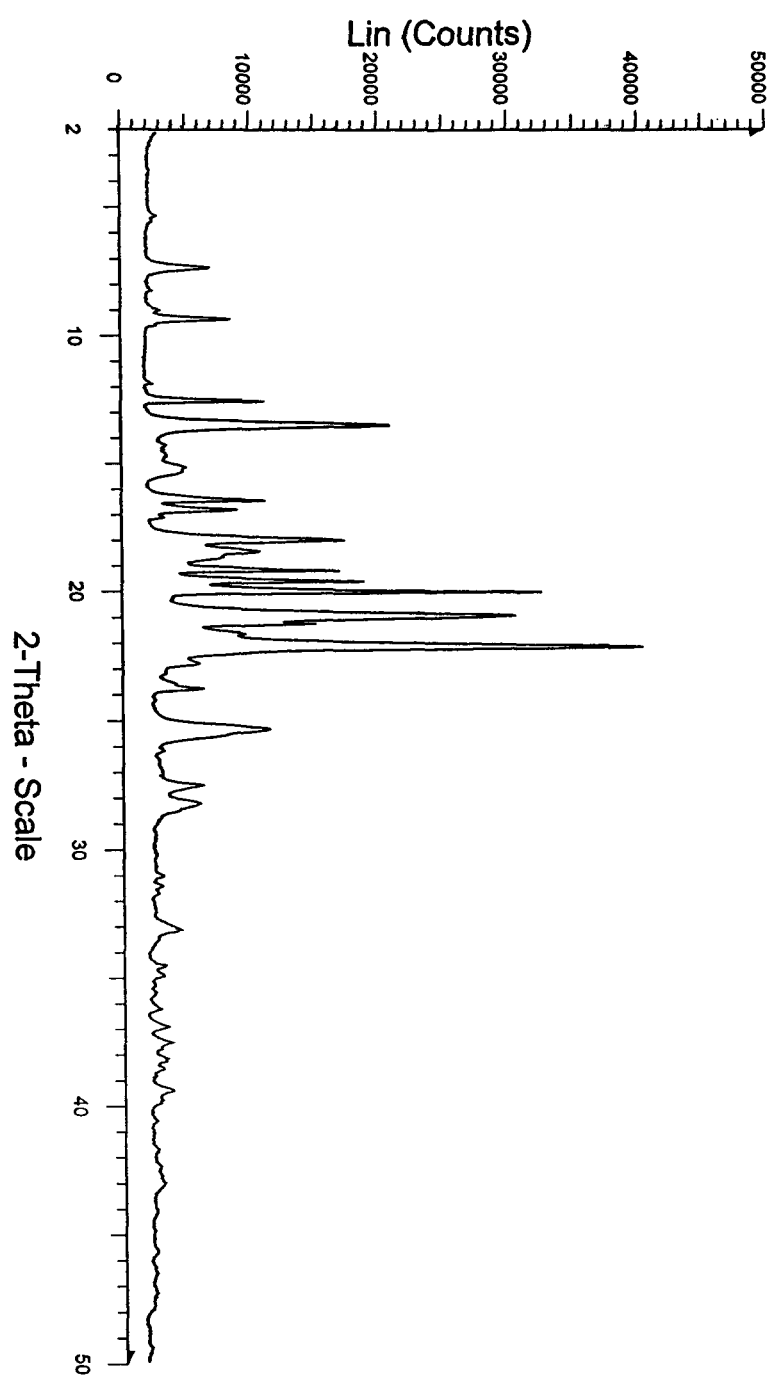
FIG. 10: XRD diffractogram of the linezolid form III pharmaceutical composition prepared by dry granulation at 60° C. for 1 month.

Stability Information:

TABLE I

Stability results of linezolid form III at room temperature, 25° C./60% RH, 40° C./75% RH and 60° C. in the compositions of examples 1-6 prepared by dry granulation.

| Examples | Interval | 25° C./60% RH | 40° C./75% RH | 60° C. |
|---|---|---|---|---|
| 1-5 | T = 0 | Form III | Form III | Form III |
| | T = 1 Month | — | Form III | Form III |
| | T = 2 Months | — | Form III | — |
| | T = 3 Months | Form III | Form III | — |

TABLE I-continued

Stability results of linezolid form III at room temperature, 25° C./60% RH, 40° C./75% RH and 60° C. in the compositions of examples 1-6 prepared by dry granulation.

| Examples | Interval | 25° C./60% RH | 40° C./75% RH | 60° C. |
|---|---|---|---|---|
| 6 | T = 0 | 85% crystallinity in Form III | 85% crystallinity in Form III | 85% crystallinity in Form III |

The results in table I shows that when dry granulation is utilized, the dosage form containing linezolid retains its polymorphic Form III.

TABLE II

Stability results of linezolid form III at room temperature using wet granulation with different concentrations of water (compositions of examples 7-9 prepared by wet granulation).

| Interval | 10% w/w of water | 20% w/w of water | 30% w/w of water |
|---|---|---|---|
| T = 0 | 100% crystallinity in Form III | 80% crystallinity in Form III | 70% crystallinity in Form III |

The results in table II reveals that the pharmaceutical composition prepared by wet granulation with 20% w/w and 30% w/w of water as granulation solvent undergoes polymorphic form conversion even at room temperature. Surprisingly, dosage form produced by wet granulating with 10% w/w of water as granulation solvent are stable to maintain its crystallinity in Form III.

The results of the above described experiments demonstrate the following:

Dry granulation (slugging) process retains the crystalline form III of linezolid in the composition.

Dry granulating linezolid form III with polacrilin potassium as disintegrant retains its polymorphic form in the dosage form as compared to other superdisintegrants such as croscarmellose sodium.

Dry granulating linezolid form III with lactose monohydrate, hydroxypropylmethyl cellulose and/or starch, polacrilin potassium and magnesium stearate enhances the stability by retaining its polymorphic form.

Wet granulating linezolid form III with 10% w/w of water as granulation solvent are stable to maintain its crystallinity in Form III.

Dry granulation is better than wet granulation to provide a stable formulation with out polymorphic form conversion.

We claim:

1. A process for preparing a stable pharmaceutical composition comprising linezolid Form III and at least one pharmaceutically acceptable excipient, comprising
    wet granulating the linezolid Form III and the pharmaceutically acceptable excipient using 10% w/w of water based on total weight of the core tablet as a granulation solvent, wherein the stable pharmaceutical composition retains more than 80% crystallinity of linezolid form III.

2. The method of claim 1, wherein the pharmaceutically acceptable excipient is sodium carboxymethyl cellulose, calcium carboxymethyl cellulose, dicalcium phosphate, sodium starch glycolate, lactose monohydrate, lactose impalpable, polacrilin potassium, polyvinylpyrrolidone, hydroxypropylmethyl cellulose, alginic acid, magnesium stearate, sodium stearyl fumarate, or colloidal silicon dioxide.

3. The method of claim 1, wherein the pharmaceutically acceptable excipient is polacrilin potassium as a disintegrant.

4. The method of claim 1, wherein the pharmaceutically acceptable excipient is hydroxypropylmethyl cellulose as a binder.

5. The method of claim 1, wherein the pharmaceutically acceptable excipient is polacrilin potassium as a disintegrant and hydroxypropylmethyl cellulose as a binder.

6. The method of claim 1, wherein the pharmaceutically acceptable excipient is a diluent and wherein the diluent is mannitol, sorbitol, xylitol, lactose monohydrate, microcrystalline cellulose, magnesium carbonate, dicalcium phosphate, tribasic calcium phosphate, or a mixture thereof.

7. The method of claim 1, wherein the pharmaceutically acceptable excipient is a lubricant and wherein the lubricant is magnesium stearate, zinc stearate, calcium stearate, sodium stearyl fumarate, stearic acid, or a mixture thereof.

8. The method of claim 1, wherein the pharmaceutical composition comprises 60% to 90% of linezolid Form III, 1% to 30% of lactose monohydrate, 0.3% to 20% of hydroxypropylmethyl cellulose, 0.2% to 8% of polacrilin potassium, and 0.5% to 5% magnesium stearate.

\* \* \* \* \*